United States Patent [19]
Christol et al.

[11] 4,317,698
[45] Mar. 2, 1982

[54] END POINT DETECTION IN ETCHING WAFERS AND THE LIKE

[75] Inventors: James T. Christol, Cupertino; John S. Burchard, Santa Clara, both of Calif.

[73] Assignee: Applied Process Technology, Inc., Santa Clara, Calif.

[21] Appl. No.: 206,490

[22] Filed: Nov. 13, 1980

[51] Int. Cl.³ ............................................. C23F 1/02
[52] U.S. Cl. .................................. 156/626; 156/345; 156/639; 156/640; 356/445
[58] Field of Search .............. 156/626, 627, 345, 640, 156/656, 659.1, 639; 356/381, 445, 448; 427/10

[56] References Cited

U.S. PATENT DOCUMENTS 4,068,016  1/1978  Wilmanns ............................ 427/10
4,161,356  7/1979  Giffin et al. ......................... 354/323
4,198,261  4/1980  Busta et al. ......................... 156/626
4,208,240  7/1980  Latos .................................. 156/627

OTHER PUBLICATIONS

IBM Technical Disclosure Bulletin, vol. 21, No. 3, Aug. 1978, Multiple Optical End-Point Detector by B. H. Desilets, pp. 1035-1037.

Primary Examiner—William A. Powell
Attorney, Agent, or Firm—Thomas Schneck

[57] ABSTRACT

A method for detecting the end point of etching wafers and the like by reflective means. Typically, a detected reflectance signal will have a threshold level representing a lack of substantial etching, a dip in the threshold level representing the commencement of etching and an inflection level representing a maximum rate of light amplitude change. The present method involves subtracting the inflection level from the threshold level and taking a predetermined fraction of the resultant level to define a second threshold level further in the etch cycle which anticipates the end of the cycle. By observational experience, the predetermined fraction can be determined. As soon as the second threshold level is reached, brakes are applied to the etching process so that etching will cease shortly after the predetermined level has been identified. In this manner, the actual end of etching will coincide with the attainment of a desired etching condition, such as removal of a layer of undesired metalization, without significant overshoot.

8 Claims, 4 Drawing Figures

END POINT DETECTION IN ETCHING WAFERS AND THE LIKE

TECHNICAL FIELD

The invention relates to the etching of coated materials and in particular to the detection of a desired end point in the etching process wherein a coating is removed.

In manufacturing semiconductor integrated circuits, silicon wafers are often coated with one or more layers of materials, some of which are etched or partially etched in the manufacturing process. For example, near the end of the integrated circuit manufacturing process, a layer of metalization, usually aluminum, is applied to establish electrical interconnections between devices and portions of devices. To remove unwanted metalization, a protective film or mask may be applied over desired regions, while undesired regions are left exposed. A chemical etchant is then applied to the exposed metalization and the exposed metal is removed. The present invention addresses the problem of stopping the etching process after the undesired metalization is removed.

BACKGROUND ART

U.S. Pat. No. 4,161,356 to J. W. Giffin, M. A. De Santis and J. S. Burchard discloses a prior art housing which has been used for chemical etching of integrated circuit wafers.

U.S. Pat. No. 4,208,240 to T. S. Latos shows a prior art etching end point detector. In this apparatus, coherent light is directed onto the surface being etched, so that changes in reflectivity of the surface upon exposure of the underlying substrate produce a detectable change in the characteristics of the reflected light. The present invention relies upon this same technique, with some important differences which are explained below. In prior art devices, it is typical that an intense light source is used to illuminate a wafer or the like from outside of the housing where etching is done. Specular reflection from the wafer is observed by a detector, usually outside the housing. The fact that both the source and the detector are outside the housing usually requires intense sources and sensitive detectors.

A first level of reflection is observed at the beginning of etching and a second level of reflection, clearly distinct from the first level, is observed with respect to the end point. After the second level is observed for a predetermined time interval, the end point is identified.

The analog electrical signal representing the amplitude of reflectance is differentiated and circuits are provided to detect the transition from one slope condition to another distinguishable slope condition.

A similar approach is taken in U.S. Pat. No. 4,198,261 to H. Busta, R. Lajos and K. Bhasin where sharply different values of light intensity are detected when a desired layer is etched and the next layer reflects a light beam at an intensity different from the former layer.

U.S. Pat. No. 4,068,016 to Wilmanns describes a reflective system for controlling build-up of thin layers of the type described above. In the aforementioned patent, the time derivative signal is compared with a reference signal and the difference is used to regulate the evaporation rate for building up thin layers.

In summary, prior art etching and evaporation control systems of the reflective type rely on the derivative of a signal representing reflectance to attain a measurably different condition relative to a prior condition. One drawback of this approach is that a finite time must pass before the different condition is recognized. In other words, in prior art systems there is a time delay which arises after a characteristic end point condition arises due to the need to verify that the condition has indeed occurred. For example, in U.S. Pat. No. 4,208,240 the end point is recognized after a zero derivative is sensed for a time interval.

An object of the present invention was to devise a reflective end point measurement method which does not require waiting a specified time for ascertaining whether the end point has been reached. A problem of waiting to verify an end point condition is that further etching is occurring which could damage underlying layers.

DISCLOSURE OF INVENTION

The above object has been met by a reflective end point measurement which anticipates the arrival of the end point. Typically, the differentiated reflectant signal will have a threshold level representing a lack of substantial etching, a dip in the threshold level representing the commencement of etching and an inflection level representing a maximum rate of light amplitude change. The present method involves subtracting the inflection level from the threshold level and taking a predetermined fraction of the resultant level to define a second threshold level further in the etch cycle which anticipates the end of the cycle. By observational experience, the predetermined fraction can be determined. As soon as the second threshold level is reached, brakes are applied to the etching process so that etching will cease shortly after the predetermined level has been identified. In this manner, the actual end of etching will coincide with the attainment of a desired etching condition, such as removal of a layer of undesired metalization, without significant overshoot.

BEST MODE FOR CARRYING OUT THE INVENTION

Figure 1:
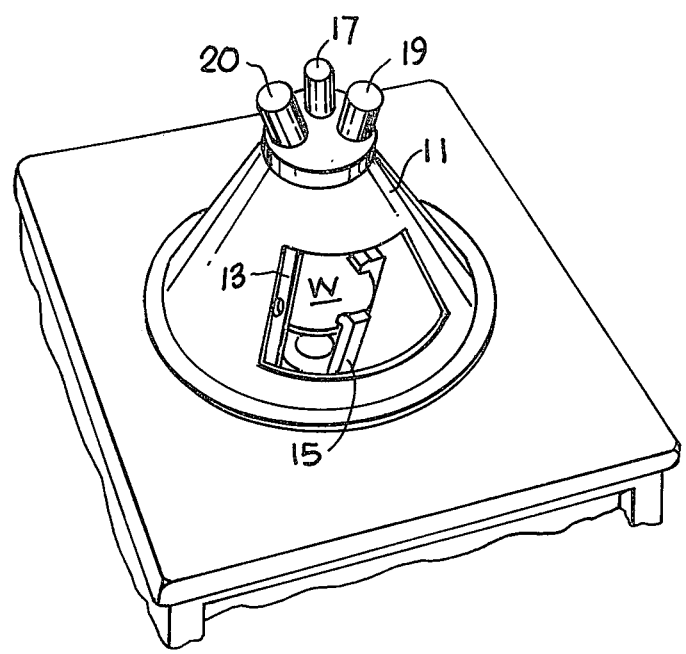
FIG. 1 is a perspective view of an etching chamber holding a light source and a light detector, as well as a wafer or similar article to be etched.

With reference to FIG. 1, an etching chamber 11 is shown, quite similar to the housing in the aforementioned U.S. Pat. No. 4,161,356. The chamber 11 has a truncated conical shape with a sliding door 13 and a wafer holder 15 which is connected to a spinner mechanism, such as a motor, not shown. Door 13 is large enough to allow entry of a human hand for removal of a wafer. In this patent application, the invention is described with reference to wafers of the type from which semiconductor integrated circuits are made. However, the invention is not restricted to any particular manufacturing process and may have application to other fields such as chemical vapor deposition, plating, and the application and removal of other thin films and materials, so long as sufficient optical contrast exists between layers being applied or removed.

The present invention relies upon diffuse reflection of a light from a light source 17 which directs polychromatic light onto a wafer W held on holder 15. Holder 15 is a centrifugal chuck wherein only edges of the wafer are contacted as the chuck rotates. Source 17 communicates directly with the inside of chamber 11, without any intervening windows or other barriers. In the prior art, it is typical to use monochromatic sources, such as lasers in order to compensate for attenuation experienced in passing through windows, as well as to achieve a strong reflected signal, primarily by specular reflection. In the present invention, such an intense source is not required because the measured reflectance is diffuse reflectance measured by light detectors 19 and 20. Although two detectors as shown, only one is needed for the measurement.

In chemical etching of a wafer the chamber 11 may contain vapors of etchants and etching by-products. It is desirable to keep the chamber closed during etching. For uniformity of processing, wafer W is usually rotated at a known rate, say six revolutions per second. The measurement described herein is preferably made once each revolution. Using this rate, the measurement will occur when the wafer is in the same position from revolution to revolution.

Light source 17 is an incandescent source having a power of a few watts and is positioned in front of a reflector which beams light downwardly onto wafer W. Chemicals for etching may be introduced through sides of the chamber by means of jets, not shown, which spray streams of etchant directly onto the wafer surface. The spinning of the wafer causes dispersal of the etchant over the wafer surface.

Figure 2:
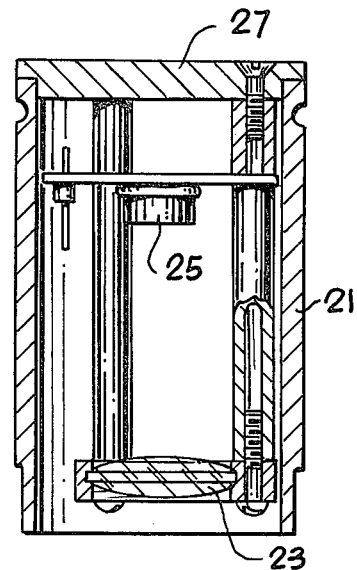
FIG. 2 is a side sectional view of a light detector used in the chamber of FIG. 1.

Light detector 19 is described in more detail with reference to FIG. 2 where the housing 21 supports a light-collecting lens 23 at the inward end of the housing and a photodiode or phototransistor 25 at the focal point of lens 23. A cover 27 is secured to the tubular body of housing 21 to maintain a light tight relation. The entire detector body is secured to chamber 11 in a similar light-tight relation so that the photodiode 25 is exposed only to diffuse reflectance from source 17. In this regard, door 13 in the chamber body is opaque and when closed provides both a light seal, as well as a chemical seal. The photodiode 25 converts an optical signal indicative of diffuse reflectance to a proportional electrical analog signal. This signal is removed by means of wires, not shown, but indicated schematically in FIG. 3.

Figure 3:
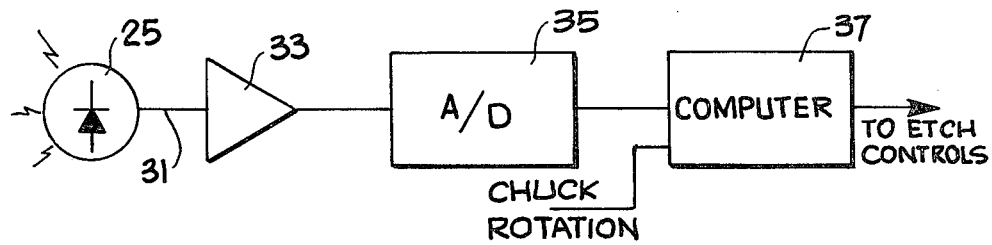
FIG. 3 is a block diagram of the signal processing electronics used in the present invention.

With reference to FIG. 3, photodiode 25 is shown to be joined by means of a wire 31 to an electrical operational amplifier 33 which amplifies the diffuse reflectance signal. Amplifier 33 is connected to an analog-to-digital converter 35 which samples the diffuse reflectance signal and provides a corresponding digital signal to a microcomputer 37. Computer 37 computes the time derivative of the diffuse reflectance signal in accord with the following digital filter equation:

$$ax_{n-2} + bx_{n-1} + cx_{n+1} + dx_{n+2} = (dy/dt) \qquad (1)$$

where (dy/dt) is the derivative of diffuse reflectance $ax_{n-2}$ is the value of instantaneous reflectance two passes prior to the measurement $bx_{n-1}$ is the value of instantaneous reflectance one pass prior to the measurement $cx_{n+1}$ is the value of instantaneous reflectance one pass subsequent to the measurement $dx_{n+2}$ is the value of instantaneous reflectance two passes subsequent to the measurement.

A signal indicative of chuck rotation is also fed to computer 37 to serve as a synchronization signal for timing measurements, such as one measurement for each chuck rotation. Although the source and detector are always on, data from the photodiode 25 should be sampled at least at the synchronization rate.

Figure 4:
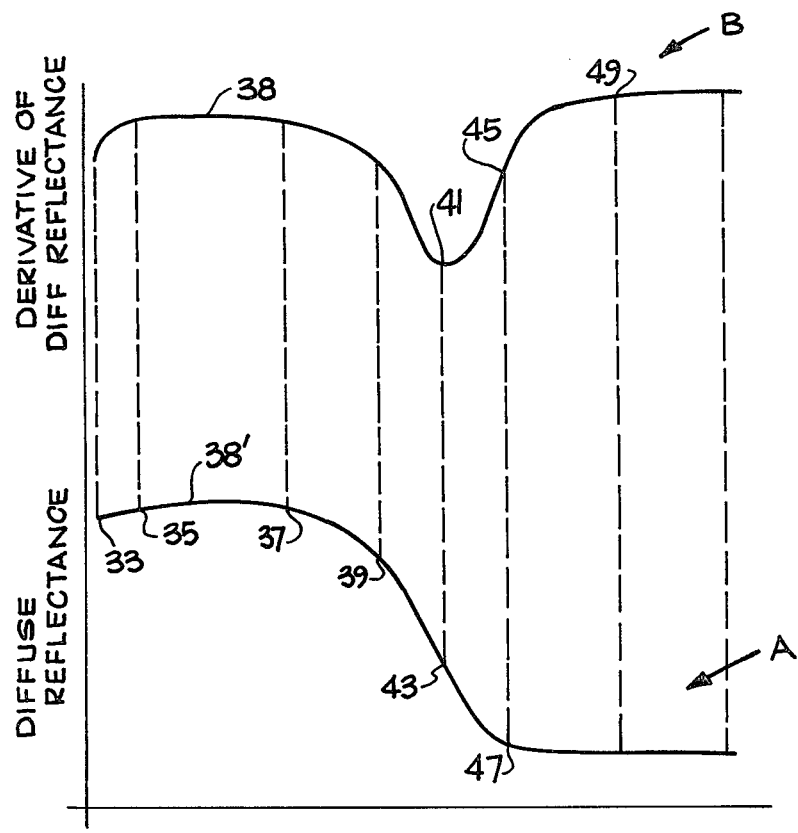
FIG. 4 shows plots of reflectance versus time and the derivative of reflectance versus time for an actual silicon wafer having a layer of aluminum metalization which was etched.

FIG. 4 shows a lower curve, A, which is a plot of diffuse reflectance for an actual semiconductor wafer. The plot has been smoothed to eliminate relatively high frequency sinusoidal oscillations. Plot A represents a typical etch cycle. Such an etch cycle is characterized by a short waiting period indicated between points 33 and 35. After this short wait for stabilization, a brief timing interval is set to run prior to any etching activity. This timing occurs between points 35 and 37. During this time, the derivative a plot A is being computed in accord with equation (1) and is shown as plot B. During this time, the computer is instructed to look for the maximum value of the derivative. This maximum 38 in the derivative plot B is used to define a threshold level 38' in plot A which is used as a reference subsequently.

To verify that etching has commenced, the computer is instructed to look for the threshold to be exceeded by a predetermined number of samples in subintervals between the points 37 and 39. Once this occurs, the computer next looks for an inflection point in the derivative, such as point 41. The inflection represents a maximum rate of light amplitude change and is indicated on plot A by point 43.

Once the inflection point 43 is identified, the etch point end can be anticipated in the following way. In this regard, the present invention differs from the prior art. A new threshold 45 in plot B is calculated by subtracting the level of inflection point 43 from the first threshold level 39. A certain percentage of that value is taken to compute a new threshold level, point 47 in plot A which corresponds to point 45 in plot B. By means of prior calibration runs, the predetermined fraction, mentioned above, is selected. Once the derivative reaches point 45 in plot B, chemical etching is drastically slowed, say by ceasing the introduction of chemicals and clearing of the etch chamber.

It will take some time for etching to completely stop and thus in plot B, the derivative of reflectance does not become flat until point 49. In the prior art, etching was not terminated until point 49 was reached, but this can cause overshoot and further etching of underlying layers. By terminating etching at point 45, or "applying the brakes", the system is allowed to "coast" to a termination of etching, without overshoot. Once point 45 is reached in plot B, the point can be defined as the end of etching or as the anticipated end of etching. In the latter case, a predetermined waiting period is added after point 45 is reached. Thus, in the latter instance point 45 is an "early warning" point which allows preparatory control actions to be taken. In either case, the present invention calls for anticipating the end of the etch cycle.

We claim:

1. A method for establishing the end point of etching major surfaces of coated reflective surfaces comprising, (a) directing light from a source onto a major surface of a coated reflective material being etched during an etch cycle, (b) detecting the amplitude of reflected light from said material and producing a first electrical signal representing the diffusely reflected light during an etch cycle, (c) using the derivative of the amplitude of reflected light to anticipate the end of etching by computing the cycle time when the etch cycle should be braked, said anticipation based upon finding the inflection level to the derivative, (d) braking the etch cycle at said cycle time.

2. The method of claim 1 wherein said coated material is rotating relative to said light and the step of detecting diffusely reflected light is performed once each revolution.

3. The method of claim 1 wherein said light directed onto said source is polychromatic light.

4. The method of claim 1 wherein said reflected light is diffusely reflected light.

5. A method for establishing the end point of etching of major surfaces of coated reflective materials comprising, (a) directing light from a source onto a major surface of a coated reflective material being etched during an etch cycle, (b) detecting the amplitude of reflected light from said material and producing a first electrical signal representing the diffusely reflected light during an etch cycle, (c) differentiating the first electrical signal and producing a second electrical signal which is electrically monitored for the following characteristics:
  (1) a first threshold level representing lack of substantial etching
  (2) a dip in the first threshold level representing commencement of etching
  (3) an inflection level representing a maximum rate of light amplitude change (d) subtracting the inflection level from the first threshold level and taking a predetermined fraction of the resultant level to define a second threshold value further in the etch cycle, (e) braking the etch cycle after the second threshold value is reached by said second electrical signal, thereby establishing the end point of etching.

6. The method of claim 5 wherein said coated material is rotating and the step of differentiating said first electrical signal is performed at least once each revolution.

7. The method of claim 5 wherein said light directed onto said source is polychromatic light.

8. The method of claim 5 wherein said reflected light is diffusely reflected light.

* * * * *